United States Patent
Yu

(10) Patent No.: US 11,224,759 B2
(45) Date of Patent: Jan. 18, 2022

(54) VITAMIN D LIGHTING SYSTEM

(71) Applicant: SIGNIFY HOLDING B.V., Eindhoven (NL)

(72) Inventor: Jianghong Yu, Best (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 372 days.

(21) Appl. No.: 16/339,182

(22) PCT Filed: Oct. 4, 2017

(86) PCT No.: PCT/EP2017/075147
§ 371 (c)(1),
(2) Date: Apr. 3, 2019

(87) PCT Pub. No.: WO2018/065443
PCT Pub. Date: Apr. 12, 2018

(65) Prior Publication Data
US 2019/0308032 A1   Oct. 10, 2019

(51) Int. Cl.
*A61N 5/06*   (2006.01)

(52) U.S. Cl.
CPC ......... *A61N 5/0616* (2013.01); *A61N 5/0618* (2013.01); *A61N 5/0613* (2013.01); *A61N 2005/063* (2013.01); *A61N 2005/0651* (2013.01); *A61N 2005/0654* (2013.01); *A61N 2005/0661* (2013.01); *A61N 2005/0665* (2013.01)

(58) Field of Classification Search
CPC .. A61N 5/0616; A61N 5/0618; A61N 5/0613; A61N 2005/063; A61N 2005/0651; A61N 2005/0654; A61N 2005/0661; A61N 2005/0665
See application file for complete search history.

(56) References Cited

U.S. PATENT DOCUMENTS

| | | | |
|---|---|---|---|
| 6,413,268 B1 * | 7/2002 | Hartman | A61N 5/0616 250/504 R |
| 2006/0082987 A1 | 4/2006 | Dorsey et al. | |
| 2008/0116401 A1 | 5/2008 | Rice et al. | |
| 2013/0172963 A1 | 7/2013 | Moffat | |
| 2014/0207215 A1 | 7/2014 | Fiset | |
| 2016/0129279 A1 * | 5/2016 | Ferolito | A61N 5/0618 607/89 |
| 2016/0303394 A1 * | 10/2016 | Hayashi | A61L 9/20 |
| 2017/0080246 A1 * | 3/2017 | Knight | A61M 21/02 |
| 2018/0180226 A1 * | 6/2018 | Van Bommel | H01L 25/0756 |

FOREIGN PATENT DOCUMENTS

| | | |
|---|---|---|
| JP | 2010146833 A | 7/2010 |
| WO | 2008129278 A2 | 10/2008 |

* cited by examiner

*Primary Examiner* — Lynsey C Eiseman
*Assistant Examiner* — Jessandra F Hough

(57) ABSTRACT

A lighting system comprises a housing, an arrangement of UV-B LEDs in the housing and a fabric output screen which provides a UV-B exit surface. This provides UV-B light for an indoor application in order to replicate the health benefits of natural sunlight.

12 Claims, 1 Drawing Sheet

VITAMIN D LIGHTING SYSTEM

CROSS-REFERENCE TO PRIOR APPLICATIONS

This application is the U.S. National Phase application under 35 U.S.C. § 371 of International Application No. PCT/EP2017/075147, filed on Oct. 4, 2017, which claims the benefit of European Patent Application No. 16192856.9, filed on Oct. 7, 2016. These applications are hereby incorporated by reference herein.

FIELD OF THE INVENTION

This invention relates to lighting systems, in particular for enabling the synthesis in the human body of vitamin D.

BACKGROUND OF THE INVENTION

People spend approximately 90% of their time indoors, a substantial amount of this at work, in an office.

However, natural sunlight is essential for the human body, for example for vitamin D production. It would therefore be desirable to have times during the working day when exposed to natural sunlight. This exposure for example would help the prevention of osteomalacia in adults. Studies have found that 90% of the population worldwide is below sufficient levels of Vitamin D, because of too limited exposure to Sunlight (UV), especially in winter time. A correlation between low vitamin D levels and the incidence of a large number of health issues has been identified, for example mood, energy, muscle weakness, cardiovascular disease, multiple sclerosis, diabetes, obesity, depression, Alzheimer's, cancers, etc.

More and more people want a better work-life balance, and would therefore appreciate exposure to more healthy lighting during the working day. In addition, increasing numbers of people take vitamin D supplements for the prevention of osteomalacia, because of the problem that artificial lighting does not enable sufficient synthesis of vitamin D.

However, it is not easy to provide natural sunlight in an office environment. There is therefore a need for a lighting system which is able to replicate the benefits of natural sunlight, but which can be used in an indoor environment, such as an office environment.

SUMMARY OF THE INVENTION

The invention is defined by the claims.

According to examples in accordance with an aspect of the invention, there is provided a lighting system, comprising:
a housing;
an arrangement of UV-B LEDs in the housing; and
a fabric output screen which provides a UV-B exit surface.

This system provides UV-B light for indoor lighting applications, such as for part of an office lighting system. The UV-B lighting may be provided in combination with general visible lighting to provide a stimulation of the health effects as well as visual illumination, preferably the system may provide the appearance of natural daylight.

The fabric output screen is at least partially transparent to UV-B light to allow the UV-B light to enter the indoor space. Fabric is not a commonly used material for UV transmission, normally material such as quartz, sapphire, ceramics or certain silicones are chosen but these have limitations when a large panel UV emitting light is desired. The fabric screen for example has a level of transparency which depends on the way the fabric is woven. This transparency is commonly expressed as a denier (D) measurement. Denier is a unit of measurement for the linear mass density of fibers and is the mass in grams of 9000 m of the fiber in question. Denier is used to determine the diameter of the fibers in the fabric. The denier is based on a natural reference, that of a single strand of silk. A single strand of silk 9000 m long weighs about 1 gram (g) and therefore is 1 denier. The higher the denier number the greater the diameter of the yarn. The linear density of yarn used in the manufacturing process also determines the perceived visual opacity of the article in the following, commonly used categories:
ultra sheer; less than 10 denier,
sheer; 10 to 30 denier,
semi-opaque; 30 to 40 denier,
opaque; 40 to 70 denier, and
thick opaque; 70 denier or higher.

For example, the fibers in a 40-denier (40D) nylon fabric have a diameter over 6.5 times greater than the diameter of the silk strand and almost 1.5 times the diameter of fibers in a 20 denier (20D) nylon fabric.

The fabric output screen is preferably at least partially opaque to visible light, giving a translucency with respect to eye visibility. The fabric has a low UV absorption coefficient because it exhibits no fluorescence or phosphorescence. This means the arrangement of UV-B LEDs is not visible and the visual appearance of the system is simply an unlit fabric screen, for example forming a panel in a modular ceiling installation. The fabric may have a pattern or visual color to match the general decor of the indoor space in which it is mounted.

The housing for example comprises a base which carries the UV-B LEDs and a side wall around the base, wherein the side wall comprises a UV reflector. This improves the output efficiency of the system.

The side wall for example comprises a polymer having embedded boron nitride particles. This reflector design can be made highly reflective to UV-B light. The reflectivity of the side walls is for example higher than 95% to the UV-B light.

The side wall for example comprises a UV-resistant silicone polymer composite with boron nitride, or a boron nitride fluoropolymer composite.

The fabric preferably comprises ultra-high-molecular-weight polyethylene fiber (UHMWPE), for example DSM Dyneema (trade mark). This material is highly transmissive to UV-B light. For purposes of comparison, so-called "tan-thru" fabrics (generally based on Lycra®) have a UV-B transparency of between 3-20%. These materials generally have a known disadvantage of having to be worn close to the skin otherwise they can appear partially see-through, especially if the wearer is between the viewer and the sun. It is also known that if such materials are held up to the light that they appear see through and only gain their perceived opacity when worn close to the skin. This makes such materials unsuitable for masking a lighting system, particularly if the material is used as a light exit window for a lighting system having an internal volume, for example, a mixing box.

The fibers in the DSM Dyneema for example, have a twine diameter of 3.3 mm and weight of 5 g/m. The fabric is woven in such way as to provide a minimum linear mass density for example of 40 to 200 denier. This means that the LEDs and components on the light engine are not visible to the human eye.

The fabric output screen for example has an area of more than 1500 cm$^2$ (e.g. 60 cm×60 cm).

The use of a fabric output screen enables a large size panel to be formed with low weight and low cost. These panels may be used as part of a modular ceiling and remain flush to the ceiling, or they may be freestanding or mounted on a wall or to a ceiling.

The UV-B Narrow Band (NB) LEDs for example have a wavelength of 280 nm to 315 nm which can be easily fine-tuned to an optimal wavelength for making vitamin D in the human body.

Each UV-B LED for example has an output power of 400 μW to 800 μW. The total number of UV-B LEDs can be for example in the range 10 to 40 in the panel.

The invention also provides a lighting installation comprising:

one or more lighting systems as defined above; and
one or more visible light luminaires.

The combination of visible and UV-B lighting provides the visual and health benefits corresponding to natural daylight.

The lighting installation for example comprises an office lighting installation.

The lighting systems may each comprise a ceiling panel and the luminaires may each comprise a ceiling panel. Alternatively, the lighting systems may comprise a freestanding divider for offices or they may be fitted to a wall or ceiling. This provides a modular system. The ceiling panel embodiment may be preferable as it remains particularly unobtrusive within an office space.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a lighting system, comprising a housing, an arrangement of UV-B LEDs in the housing and a fabric output screen which provides a UV-B exit surface. This provides UV-B light for an indoor application in order to replicate the health benefits of natural sunlight.

Figure 1:
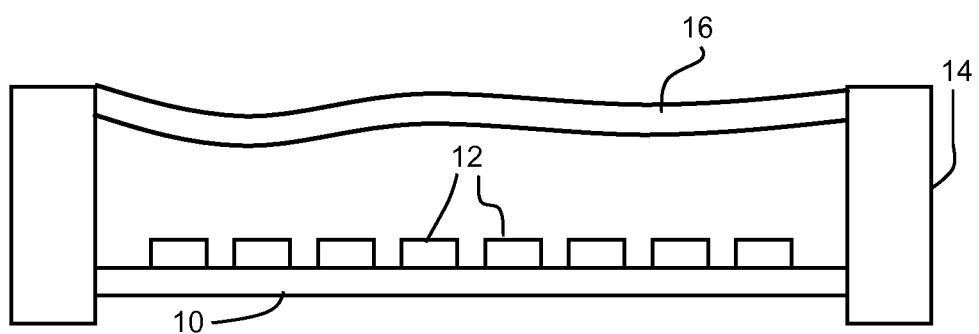
FIG. 1 shows a UV-lighting system.

FIG. 1 shows a UV-lighting system.

The system comprises a carrier 10 on which an arrangement of UV-B LEDs 12 is provided. The carrier 10 for example comprises a printed circuit board (PCB), and the UV-B LED are surface mount packages for mounting on the PCB.

A side wall 14 forms a housing together with the carrier 10 and the UV-B LEDs 12 provide UV light outwardly, normally away from the carrier 10. The housing may be any desired shape, such as rectangular, square or circular. The housing has a low profile so that it may be integrated into a ceiling structure for example. Alternatively, it may for a light fitting to be suspended below a ceiling.

The housing is closed opposite the carrier 10 by a fabric sheet 16.

The fabric sheet 16 can be produced at low cost, low weight and with large area. For example the overall system may have a size of around 45 cm×45 cm or 60 cm×60 cm. In this way it may form a panel of a modular lighting system.

Generally, the size is more than 1500 cm$_2$, for example more than 2000 cm$^2$ for example more than 3000 cm$^2$.

In a preferred example, the fabric sheet comprises fibers of ultra-high-molecular-weight polyethylene (known as UHMWPE or UHMW). This material is a type of thermoplastic polyethylene with extremely long chains, with a molecular mass usually between 3.5 and 7.5 million atomic mass units. The longer chain serves to transfer load more effectively to the polymer backbone by strengthening intermolecular interactions. This results in a very tough material.

UHMWPE fibers are for example commercially available from the chemical company DSM (trade mark), under the trade name Dyneema (trade mark). When formed into fibers, the polymer chains for example attain a parallel orientation greater than 95% and a level of crystallinity from 39% to 75%.

It is known that UHMWPE is very resistant to UV radiation (as well as to water, moisture, most chemicals and micro-organisms).

The use of UHMWPE fibers in this application is based on the recognition that the fibers are highly (compared to other fibers) transparent to UV light.

The fibers for example have a diameter in the range 2 mm to 5 mm for example a twine diameter of 3.3 mm and weight of in the range 2 to 10 g/m. The fabric is woven in such way as to provide a minimum linear mass density for example of 40 to 200 denier.

The fabric is then opaque or translucent to light in the visible light spectrum so that the LEDs 12 and other components are not visible to the human eye.

By way of example, the fibers have an axial refractive index of 1.59 and a transverse refractive index of 1.53, hence a birefringence of 0.06. They are also highly transparent to infrared, near infrared and radar.

The resulting fabric is for example at least 80% transmissive to UV light, preferably at least 90% transmissive and preferably at least 98% transmissive.

The resulting structure is also opaque (or translucent) to visible light so that the visual appearance of the UV-B LED array is masked. The screen may have a desired visual color and/or pattern, selected for consistency with the decor of the indoor space in which the system is to be used.

The side wall 14 is formed or a boron nitride powder filled polymer. The polymer is for example a silicone or fluoropolymer.

This provides a structure which is highly reflective to UV-B light. For example, a reflection may be achieved of 95% or higher.

The UV-B LEDs are designed to provide a dose of UV-B light which is sufficient to provide the advantages of vitamin D production, but not sufficient to cause skin damage. By way of example, the light intensity of the system as a whole is based on each UV-B LED having an output power of 400 μW to 800 μW. The total number of UV-B LEDs can be for example in the range 10 to 40 in the panel, giving a total output power in the range 4 mW to 30 mW.

UV-B LEDs are commercially available, and are mainly used in medical applications, for example for medical photometry. There are also commercially available UV-B lighting products for stimulating plant growth for illuminating terrariums. The UV-B wavelength is in the range 280 nm to 315 nm.

Figure 2:
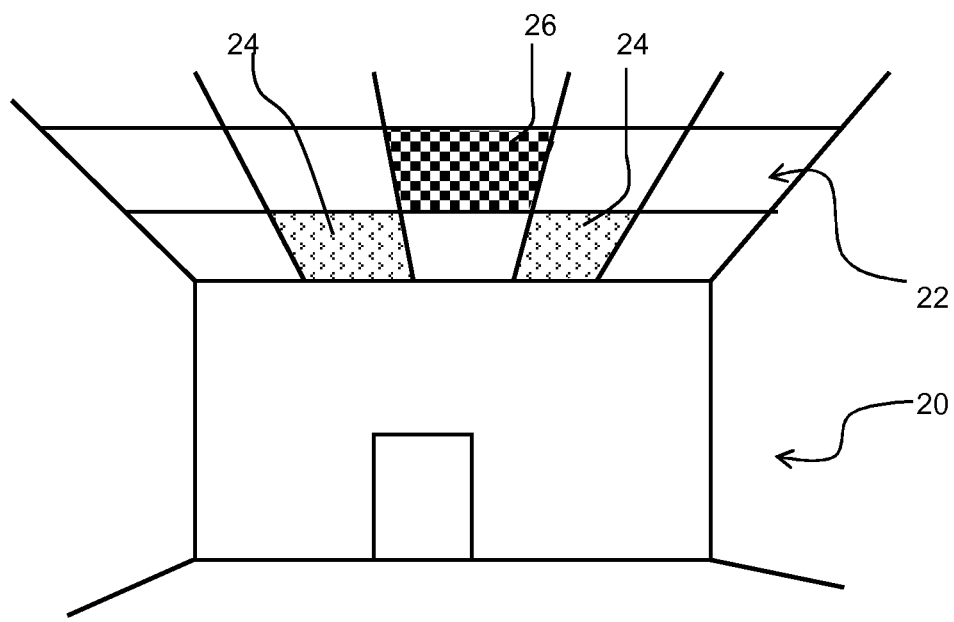
FIG. 2 shows an office space with a ceiling having visible lighting and UV-B lighting.

FIG. 2 shows an office space 20 with a ceiling 22 having visible lighting panels 24 (luminaries) and UV-B lighting panels 26 each of the type as described above. In combination, the panels provide the visual lighting required as well as a desired level of UV-B radiation.

The system may be used as part of an office lighting system, but it may also be used for other indoor lighting applications.

The example above makes use of a panel which is dedicated to the generation of UV-B radiation. It is also possible to combine UV-B radiation and visible lighting in the same panel. In such a case, a visually transparent (but typically diffusive) fabric is required so that both UV and visible light can escape from the panel. A diffusive fabric will again mask the appearance of the LED structure beneath.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An indoor lighting panel for mounting on a wall or to a ceiling, wherein the indoor lighting panel comprises:
   a housing;
   an arrangement of UV-B LEDs in the housing; and
   a fabric output screen which provides a UV-B exit surface,
   wherein the fabric output screen is at least partially transparent to UV-B light,
   wherein the fabric output screen has a linear mass density of between 40 and 200 denier, wherein the fabric output screen is at least partially opaque to visible light, and
   wherein the fabric of the fabric output screen exhibits no fluorescence or phosphorescence upon absorption of UV-B light.

2. An indoor lighting panel as claimed in claim 1, wherein the housing comprises a base which carries the UV-B LEDs and a side wall around the base, wherein the side wall comprises a UV reflector.

3. An indoor lighting panel as claimed in claim 2, wherein the side wall comprises a polymer having embedded boron nitride particles.

4. An indoor lighting panel as claimed in claim 3, wherein the polymer comprises silicone or a fluoropolymer.

5. An indoor lighting panel as claimed in claim 1, wherein the fabric of the fabric output screen comprises ultra-high-molecular-weight polyethylene fibers.

6. An indoor lighting panel as claimed in claim 5, wherein the ultra-high-molecular-weight polyethylene fibers have a diameter in the range 2 mm to 5 mm.

7. An indoor lighting panel as claimed in claim 1, wherein the fabric output screen has an area of more than 1500 $cm^2$.

8. An indoor lighting panel as claimed in claim 1, wherein the arrangement of UV-B LEDs comprises between 10 and 40 LEDs.

9. An indoor lighting panel as claimed in claim 8, wherein each UV-B LED has an output power in the range 400 µW to 800 µW.

10. A lighting installation comprising:
    one or more indoor lighting panels as claimed in claim 1; and
    one or more visible light luminaires.

11. A lighting installation as claimed in claim 10, comprising an office lighting installation.

12. A lighting installation as claimed in claim 11, wherein the indoor lighting panels each comprise a ceiling panel, and wherein the visible luminaires each comprise a ceiling panel.

* * * * *